United States Patent [19]

Kendall-Tobias

[11] Patent Number: 4,606,718
[45] Date of Patent: Aug. 19, 1986

[54] METHOD AND APPARATUS FOR SHUTTING DOWN THE BURNER OF A FLAME ATOMIC ABSORPTION

[75] Inventor: Michael W. Kendall-Tobias, Danbury, Conn.

[73] Assignee: The Perkin-Elmer Corporation, Norwalk, Conn.

[21] Appl. No.: 670,712

[22] Filed: Nov. 13, 1984

[51] Int. Cl.[4] .............................................. F23N 5/00
[52] U.S. Cl. .......................................... 431/6; 431/33; 356/315; 356/417
[58] Field of Search ............................. 431/6, 33, 126; 356/315, 417

[56] References Cited

U.S. PATENT DOCUMENTS 3,695,812 10/1972 Herron et al. .

Primary Examiner—Carroll B. Dority, Jr.
Attorney, Agent, or Firm—Francis L. Masselle; Edwin T. Grimes; Thomas P. Murphy

[57] ABSTRACT

The flame in a flame atomic absorption spectrophotometer is shut down while using nitrous oxide as the oxidant, without shifting to a different oxidant such as air, by flooding the burner with a substantial excess of nitrous oxide to blow out the flame.

17 Claims, 2 Drawing Figures

METHOD AND APPARATUS FOR SHUTTING DOWN THE BURNER OF A FLAME ATOMIC ABSORPTION

BACKGROUND

The present invention particularly relates to a flame atomic absorption spectrophotometer of the type which requires air as a start-up and shut-down oxidant and uses nitrous oxide as a high energy oxidant for the burner flame.

In atomic absorption spectroscopy, the measurement of the absorption of a radiation beam at a characteristic resonant spectral line for a particular element yields a measure of the concentration of that element in an original sample solution. At the present time, one of the most common techniques for atomizing an element for purposes of the absorption measurement is by introducing a liquid sample solution of the element of interest into a gas burner wherein droplets of the solution are vaporized and the elements ultimately atomized, so as to form in the path of the apparatus radiation beam, a substantial quantity of the element of interest in its atomic state. A sample light beam, which originates from a line-emitting light source, and which includes a resonance line of the element to be measured, is directed through the flame. The desired element in the sample absorbs the resonance lines characteristic of the element and the emerging light beam is directed to a monochromator and thence to a detector which measures the degree to which the desired element absorbs the resonance lines of the sample beam. This absorption degree represents the amount of desired element in the sample substance.

In such spectrophotometers, in order to produce a flame which has a high enough temperature for the best measurement results for certain elements, it is preferred to use acetylene gas as a fuel and to use nitrous oxide ($N_2O$) as the source of oxygen for the combustion of the acetylene gas. In order to initiate combustion in a safe manner, it is necessary to begin combustion of the acetylene gas using air as the oxygen source, and to then switch over to the nitrous oxide after the acetylene gas flame is ignited and stable.

It is also a characteristic of such a system that, in order to shut down the system in a safe manner which avoids the risk of explosions, it is customary to change back from nitrous oxide as the oxidant to air as the oxidant before turning off the burner system. This has always necessitated the provision of some means for assuring that there would be a source of air under pressure available when shut-down of the system is to be effected. Otherwise, failure of the air supply system leaves the operator with no safe means of shut-down. One common procedure for assuring the presence of an emergency air supply is to provide an accumulator container of compressed air which is kept in reserve for such a contingency. However, the necessity for an accumulator creates considerable added expense and complexity, and an increase in the size of the apparatus.

Accordingly, it is one object of the present invention to provide for a safety shut-down of the flame of the spectrophotometer without requiring the expense and complication of a compressed air accumulator container.

Another problem in accomplishing a safe shut-down of the system arises if there is a failure of electrical power. This is a problem because the spectrophotometer requires electrical power for normal productive operation, and should be shut down if the power fails. Furthermore, the controls for the burner system are electrically actuated, particularly the normal shut-down routine controls which shift the operation of the system from nitrous oxide back to air as the oxidant, and then shut the system down from that condition. Accordingly, in present flame atomic absorption spectrophotometer systems, it is necessary to provide for at least a short period of maintenance of power on the system in case of main power failure. Such power maintenance must be provided by means of standby batteries, or by means of large storage capacitors which are capable of maintaining power for a period sufficient to accomplish a safe shut-down.

Accordingly, it is another important object of the invention to provide for a safety shut-down of the flame of the spectrophotometer in case of a failure of electrical power for the spectrophotometer system.

A further object of the invention is to provide for a safety shut-down of the flame of the spectrophotometer in case of a simultaneous failure of electrical power and air pressure for the spectrophotometer system.

Further objects and advantages of the invention will be apparent from the following description and the accompanying drawings.

SUMMARY OF THE INVENTION

In carrying out the present invention there is provided an improved method for shutting down the flame in a flame atomic absorption spectrophotometer while using nitrous oxide as the oxidant without shifting to a different oxidant such as air, comprising flooding the burner with a substantial excess of nitrous oxide to blow out the flame.

DETAILED DECRIPTION OF THE DRAWINGS

DESCRIPTION OF PREFERRED EMBODIMENTS

Figure 1:
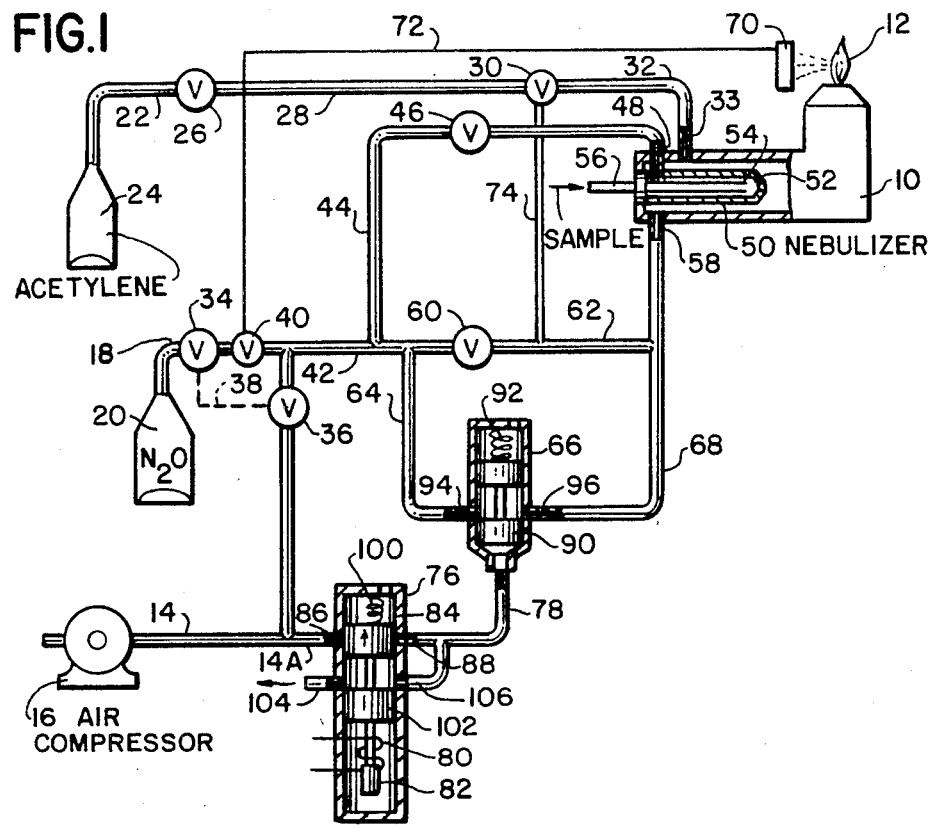
FIG. 1 is a schematic diagram of an apparatus for carrying out the present invention.

Referring particularly to FIG. 1, there is illustrated a burner 10 for a flame atomic absorption spectrophotometer, with the flame being illustrated at 12. In a typical arrangement, the apparatus includes a compressed air conduit 14 for receiving compressed air from a compressed air source such as an air compressor indicated at 16, a nitrous oxide conduit 18 connected to receive nitrous oxide from a pressurized container 20, and a fuel conduit 22 connected to receive fuel, such as acetylene gas, from a pressurized cannister 24. The fuel is supplied to the burner 10 through a control valve 26, a conduit 28, a shut-off valve 30, a conduit 32 and a burner port 33.

The burner 10 is supplied with oxidant consisting of air from the air compressor 16 or nitrous oxide from the container 20. During start-up and shut-down of the burner, air is used, and during normal running of the burner, nitrous oxide is used. A switch-over valve system shown schematically as consisting of two valves 34 and 36, with an interconnection between the valves at 38 is employed to substantially simultaneously shut off the air at valve 36 and turn on the nitrous oxide at valve 34 when the changeover from air to nitrous oxide is to take place. Various other arrangements may be employed for accomplishing this switchover valving operation, including a single valve having a single outlet, and two alternative inlets. A preferred arrangement for such a changeover valving arrangement is illustrated in a co-pending patent application Ser. No. 670,714 for an IMPROVED SYSTEM FOR CHANGING OXIDANTS IN A FLAME ATOMIC ABSORPTION SPECTROPHOTOMETER filed by the inventor of the present invention on the same date as the present application and assigned to the same assignee as the present invention.

The nitrous oxide oxidant is supplied through valve 34 and a shut-off valve 40 to a conduit 42. Compressed air is supplied through valve 36 to conduit 42.

From there, the oxidant, either air or nitrous oxide, is supplied through a conduit 44, a control valve 46, and a main port 48 to the burner 10. The oxidant at port 48 is supplied specifically to a nebulizer 50 which forms a part of the burner 10. The nebulizer 50 includes a nozzle 52 and an aspirator tube 54 through which a liquid sample including the material to be analyzed is supplied through an inlet 56.

An auxiliary port 58 is also provided for the introduction of oxidant into the burner 10. The Auxiliary port 58 may be in constant use, during burner operation, receiving oxidant through a control valve 60 and a conduit 62. However, this oxidant branch conduit 62 and valve 60 to the auxiliary port provide for only a restricted flow of oxidant, and in some embodiments, the conduit 62 and valve 60 may be omitted entirely. All of the normal oxidant flow is then provided through main port 48.

As previously mentioned above, it is customary and preferable to switch from nitrous oxide back to air by means of the valves 34 and 36 whenever the system is to be shut down, in order to avoid explosions. Accordingly, the continued availability of air from the air compressor 16 is extremely important.

In accordance with the present invention it has been discovered that, if it is necessary because of a loss of air pressure, or for other reasons, to shut down the burner without the use of air, the burner may be flooded with nitrous oxide to safely blow out the flame. This may be accomplished by means of a conduit 64, a pneumatic valve 66, and a conduit 68 which are connected to the auxiliary port 58. The substantial excess of nitrous oxide simply blows out the flame 12 in an action which is essentially analogous to that of a human when blowing out a candle. Thus, the system is shut down safely without an explosion. Further enhancing the safety of the system, the apparatus preferably includes a flame sensor 70, which is connected by means of a wire 72 to control an electrically operated shutoff valve 40. If the flame sensor 70 ceases to detect a flame, the valve 40 shuts off the nitrous oxide supply automatically. When that occurs, the lack of oxidant pressure in conduit 42 is detected through a pressure control connection 74 to shut off the valve 30 to thereby stop the supply of fuel through conduit 32 to the burner 10. Thus, fuel and oxidant are both turned off after the flame is extinguished, completely and safely shutting down the burner apparatus.

The feature including the control of valve 30 to stop the supply of fuel upon the discontinuance of oxidant pressure as detected through the pressure control connection 74 forms a part of the subject matter disclosed and claimed in a co-pending patent application entitled "Safety Apparatus for and Automatic Absorption Spectrophotometer", Ser. No. 670,711, filed Nov. 13, 1984, now U.S. Pat. No. 4,568,267 by the present applicant and assigned to the same assignee as the present application.

The conduit 68, (in combination with conduit 64 and valve 66) through which the burner 10 is flooded with nitrous oxide for emergency shut-down may be referred to as an auxiliary conduit.

Since the normal procedure for safe shut-down of the burner involves switching back to compressed air as the oxidant, the failure of the compressed air supply is an important circumstance which requires an emergency shut-down procedure. Accordingly, it is a preferred feature of the present invention to actuate the valve 66 in response to a loss of compressed air pressure which is supplied through the compressed air conduit branch 14A, a valve 76, and a conduit 78. The valve 76 is an electromagnetically operated valve schematically illustrated as actuated by means of a winding 80 which operates upon a solenoid core 82 to move the piston, including a piston land 84, upwardly to uncover the associated ports 86 and 88 to interconnect the conduits 14A and 78. The mode of operation and the purpose of valve 76 is further described below.

The valve 66 is schematically illustrated as including a piston having a piston land 90 which is spring biased by a spring 92 into the open position shown. However, under normal operation of the system, when the compressed air pressure is available on conduit 78, the piston including land 90 is moved upwardly against the bias of the spring 92 to cover the associated valve ports 94 and 96, and to thus close off the auxiliary conduit 68. However, upon a reduction of the air pressure below a safe level for a normal shut-down using air as the oxidant, the pressure is insufficient to maintain the piston of valve 66 in the raised position against the bias of spring 92, and the valve opens, flooding the burner with nitrous oxide and blowing out the flame. Thus, there is avoided the necessity for having a compressed air accumulator tank, or a standby compressor, or other means for providing compressed air for the normal shut-down procedure in case of a disablement of the compressed air system. Furthermore, such a disablement of the compressed air system may be of a nature which is not guarded against by the presence of an accumulator, such as a major rupture in the air supply line downstream from the compressor and the accumulator. The present invention overcomes that problem by accomplishing a safe shut-down upon loss of air pressure in the downstream end of the compressed air system, no matter what the cause.

The valve 66, responding as it does to air pressure, may be said to "monitor" the air pressure through the control connection conduit 78.

Referring again to the solenoid actuated valve 76, that valve may be gravity biased to the open position, or it may preferably include a biasing spring indicated at 100. The valve may preferably include an additional land 102, and a discharge port 104, and a port 106 connecting to conduit 78. As shown in the drawing, when the valve 76 is in its unenergized position, the ports 86 and 88 are closed off, and the ports 106 and 104 are opened by the land 102 to relieve any pressure in the conduit 78, and to allow valve 66 to be biased to the open position. However, upon energization of the winding 80 of the solenoid core 82, the piston of valve 76 rises so that land 102 closes ports 104 and 106, as it opens ports 86 and 88 so that conduit 78 is pressurized.

The electrical signal for the winding 80 may be obtained from any suitable source which might be used for the control of emergency shut-down. In a preferred embodiment, the winding 80 is simply connected to the main power source for the flame atomic absorption spectrophotometer, so that upon loss of power, the burner is automatically shut down by closing the ports 86 and 88 of valve 76, and opening the ports 104 and 106 to pressurized conduit 78 to allow valve 66 to open to flood the burner 10 with nitrous oxide.

If a shut-down in response to electrical failure is not desired or not needed, the valve 76 can simply be omitted from the system.

Furthermore, while not preferred, the system may be adapted to respond only to electrical failure to provide for emergency shut-down by providing electrical actuation rather than pneumatic actuation of valve 66. Such an arrangement is logical where an electrically driven air compressor 16 is used, since the most likely cause for loss of air pressure is loss of power to the air compressor drive motor.

Various commercially available valves may be used in the present system. One acceptable source for the pressure sensitive valve 66 and the solenoid valve 76 is the Clippard Instrument Laboratory, Inc., 7390 Colerain Road, Cincinnati, Ohio 45239.

Figure 2:
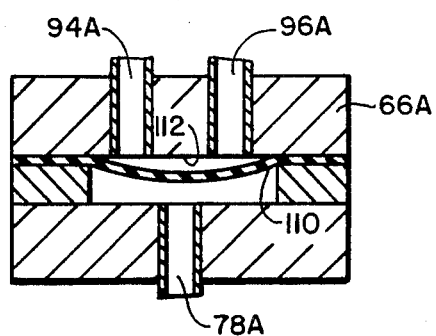
FIG. 2 is a cross-section detail view of an alternative valve structure which may be used to detect the loss of compressed air pressure.

FIG. 2 illustrates a sectional view of another alternative embodiment for the valve 66 which is identified in the drawing as 66A. Parts in valve 66A which correspond to parts in valve 66 are similarly numbered, but with the suffix letter A. Valve 66A may be referred to as a diaphragm valve, and includes a diaphragm 110 of a rubber, or rubber-like, material which is normally positioned and arranged to abut against an interior face 112 of the valve. When the air pressure at the port 78A is sufficient to equal or exceed the nitrous oxide pressure at port 94A, the diaphragm 110 is forced to remain flat against the face 112, blocking the ports 94A and 96A, and preventing flow of nitrous oxide through those ports. However, upon a decrease, or complete failure, of air pressure at port 78A, the diaphragm 110 becomes distended, as illustrated in FIG. 2, opening the ports 94A and 96A, and permitting the nitrous oxide to flood the burner 10 through the auxiliary conduit 68. The parts of valve 66A are held together by fastening means (not illustrated).

The material of the diaphragm 10 may be referred to below as "rubber-like", and that term is understood to include rubber itself, as well as other rubber-like materials.

While this invention has been shown and described in connection with particular preferred embodiments, various alterations and modifications will occur to those skilled in the art. Accordingly, the following claims are intended to define the valid scope of this invention over the prior art, and to cover all changes and modifications falling within the true spirit and valid scope of this invention.

What is claimed is:

1. An improved method for shutting down a burner system in a flame atomic absorption spectrophotometer while using nitrous oxide as the oxidant for a fuel without shifting to a different oxidant such as air which is used for iniating the flame atomic absorption spectrophotometer, comprising flooding the burner with a substantial excess of nitrous oxide to blow out the flame in response to either failure of electrical means controlling the burner system or a decrease in pressure of the different oxidant.

2. A method as claimed in claim 1 wherein the flooding of the burner with a substantial excess of nitrous oxide is carried out through an auxiliary conduit for carrying the nitrous oxide to the burner.

3. A method as claimed in claim 1 for use where the burner system which is normally shut down using air as the oxidant and wherein a source of compressed air is provided, the method including the steps of monitoring the air pressure from the compressed air source and flooding the burner with a substantial excess of nitrous oxide to blow out the flame only upon a detected reduction of air pressure below a safe level for a normal shutdown using air as the oxidant.

4. A method as claimed in claim 1 wherein a source of compressed air is provided, the method including the steps of monitoring the air pressure from the compressed air source and flooding the burner with a substantial excess of nitrous oxide to blow out the flame upon a detected reduction of air pressure below a safe level for a normal shutdown using air as the oxidant so that the flame is extinguished either upon power failure or upon reduction of the compressed air below a safe level.

5. A method as claimed in claim 4 wherein the flooding of the burner with a substantial excess of nitrous oxide is carried out through an auxiliary conduit for carrying the nitrous oxide to the burner, and wherein the air pressure is monitored by the use of a pneumatic valve arranged in the auxiliary conduit which is operable to open to permit the flooding of the burner with nitrous oxide upon the failure of air pressure, and wherein the monitoring for the presence of electric power is carried out by an electrically actuated valve connected to transmit air pressure from the compressed air source to the pneumatic valve in the presence of electric power and to disconnect the air pressure from the pneumatic valve upon the failure of electric power.

6. An improved apparatus for shutting down the burner system in a flame atomic absorption spectrophotometer while using nitrous oxide as the oxidant without shifting to a different oxidant such as air, comprising, a burner for the flame including a primary conduit connected to a source of nitrous oxide, and means for flooding the burner with a substantial excess of nitrous oxide to blow out the flame, said flooding means comprising; an auxiliary conduit for carrying the nitrous oxide to the burner, a valve in said auxiliary conduit operable to open and release nitrous oxide to blow out the flame when required, and means for monitoring for the presence of electric power on the burner system of the spectrophotometer, said monitoring means being connected to open said valve upon the failure of electric power.

7. Apparatus as claimed in claim 6 for use with a flame atomic absorption spectrophotometer which is normally shut down using air as the oxidant and wherein a source of compressed air is provided, the apparatus including means for monitoring the air pressure from said compressed air source and connected and operable to open said valve means to blow out the flame upon a detected reduction of air pressure below a safe level for a normal shutdown using air as the oxidant.

8. Apparatus as claimed in claim 7 wherein said valve and said means for monitoring the air pressure are combined in a single pressure actuated valve structure which is biased to the open position and which includes a control connection for monitoring the compressed air pressure and which is operable to the closed condition in response to the presence of sufficient compressed air pressure.

9. Apparatus as claimed in claim 7 wherein said valve and said means for monitoring air pressure are combined in a single pressure actuated valve structure comprising a housing having a pressure chamber and three ports into said chamber, two of said ports entering said chamber through a first wall of said chamber and being connected in series in said auxiliary conduit, a diaphragm of rubber-like material arranged against said first wall of said chamber, a third one of said ports of said valve communicating with said chamber through a second wall of said chamber and being connected to monitor the air pressure from said compressed air source, said diaphragm being operable to be flattened and distended in response to the balance of pressures as conveyed through said ports from said auxiliary conduit and from said compressed air source to open and close the connection between said first and second ports in said common wall in response to said balance of pressures to thereby provide for substantial flow of nitrous oxide through said first and second ports upon reduction of air pressure in said third port.

10. Apparatus as claimed in claim 6 for use with a flame atomic absorption spectrophotometer which is normally shut down using air as the oxidant and wherein a source of compressed air is provided, the apparatus including means for monitoring the air pressure from said compressed air source and combined with said valve and operable to open said valve to blow out the flame upon a detected reduction of air pressure below a safe level for a normal shutdown using air as the oxidant so that the flame is extinguished either upon power failure or upon reduction of the compressed air below a safe level.

11. Apparatus as claimed in claim 10 wherein said combined air pressure monitoring means and valve comprise a pneumatic valve arranged in the auxiliary conduit which includes connection to sense air pressure and which is operable to open to permit the flooding of the burner with nitrous oxide upon the failure of air pressure, an electrically actuated valve connected to transmit air pressure from the compressed air source to said pneumatic valve in the presence of electric power and to disconnect the air pressure from said pneumatic valve upon the failure of electric power.

12. A safety burner apparatus for a flame atomic absorption spectrophotometer of the type which requires air as the start-up and shutdown oxidant and uses nitrous oxide as a high energy oxidant for a burner flame comprising a burner including a nebulizer having a main oxidant port therein, a conduit connection to selectively carry either air or nitrous oxide oxidant to said main oxidant port, said burner including a fuel port for receiving a fuel such as acetylene, an auxiliary oxidant port, an auxiliary conduit connected for carrying nitrous oxide to said auxiliary port while nitrous oxide is the selected oxidant, said auxiliary conduit including a controllable valve which is biased to the open position, a control connection from said valve arranged for connection to a source of air under pressure to be used as an oxidant, said valve being operable to remain closed in the presence of air pressure and to open upon the failure of air pressure to provide a substantially unrestricted flow of nitrous oxide through said auxiliary port to extinguish the burner flame.

13. An apparatus as claimed in claim 12 wherein there is provided an electrical solenoid operated valve normally biased to the closed position and connected in said control connection from said first named valve for receiving air under pressure, said solenoid valve being arranged for connection to the electrical power source supplying power to the atomic absorption spectrophotometer to maintain said solenoid valve in an open position to supply compressed air to said first named valve as long as electrical power is present, and said solenoid valve being operable to close upon the cessation of electrical power to thereby discontinue the supply of compressed air to said first named valve to cause said first named valve to open to thereby extinguish the flame upon failure of electrical power.

14. Apparatus as claimed in claim 12 wherein there is provided a transfer valve means to switch the oxidant from air to nitrous oxide on start up and to switch the oxidant from nitrous oxide to air for normal shutdown.

15. Apparatus as claimed in claim 12 wherein a volume control valve is connected in said conduit connection for carrying oxidant to said main oxidant port for adjusting the volume of oxidant flow.

16. Apparatus as claimed in claim 12 wherein there is provided a flame sensor arranged to sense the presence of a flame in the flame atomic absorption spectrophotometer and an electrically operated valve connected for operation in response to signals from said flame sensor and operable to shut off the flow of nitrous oxide oxidant to said burner upon the discontinuance of the flame.

17. Apparatus as claimed in claim 16 including a fuel conduit connected for carrying fuel to said fuel port, a fuel control valve arranged in said fuel conduit, said fuel control valve including a control connection to detect the presence of oxidant pressure downstream from said flame detector controlled valve, and said fuel control valve being operable upon the loss of oxidant pressure to shut off the flow of fuel through said fuel conduit and through said fuel port.

* * * * *